US012690917B2

(12) United States Patent
Hagstrom et al.

(10) Patent No.: US 12,690,917 B2
(45) Date of Patent: ***Jul. 28, 2026

(54) WIDE AREA FOCAL ABLATION CATHETER

(71) Applicant: Boston Scientific Scimed, Inc., Maple Grove, MN (US)

(72) Inventors: Nathan Paul Hagstrom, Minneapolis, MN (US); Emily Rose Whitwam, Blaine, MN (US); Joel T. Eggert, Plymouth, MN (US); Jason John Matteson, Jr., Beldenville, WI (US)

(73) Assignee: Boston SCIENTIFIC Scimed, Inc., Maple Grove, MN (US)

( * ) Notice: Subject to any disclaimer, the term of this patent is extended or adjusted under 35 U.S.C. 154(b) by 61 days.

This patent is subject to a terminal disclaimer.

(21) Appl. No.: 18/634,785

(22) Filed: Apr. 12, 2024

(65) Prior Publication Data

US 2024/0341843 A1     Oct. 17, 2024

Related U.S. Application Data

(60) Provisional application No. 63/496,080, filed on Apr. 14, 2023.

(51) Int. Cl.
A61B 18/14     (2006.01)
*A61B 18/00*     (2006.01)

(52) U.S. Cl.
CPC .............................. A61B 18/1492 (2013.01); *A61B 2018/00351* (2013.01); *A61B 2018/00577* (2013.01);
(Continued)

(58) Field of Classification Search
CPC ...... A61B 18/1492; A61B 2018/00267; A61B 2018/00351; A61B 2018/00577;
(Continued)

(56) References Cited

U.S. PATENT DOCUMENTS 9,655,677 B2 * 5/2017 Salahieh ................ A61B 5/287
2003/0225403 A1 12/2003 Woloszko et al.
(Continued)

OTHER PUBLICATIONS

International Search Report and Written Opinion for PCT Application No. PCT/US2024/024490 mailed Aug. 20, 2024. 15 pages.

*Primary Examiner* — Michael F Peffley
(74) *Attorney, Agent, or Firm* — Nelson Mullins Riley & Scarborough LLP

(57)          ABSTRACT

A catheter for ablating cardiac tissue through irreversible electroporation, the catheter comprises a tubular outer shaft and an electrode assembly extending distally from the distal end of the outer shaft. The electrode assembly defines a distally located central hub portion and a plurality of splines each extending proximally from the central hub portion. The electrode assembly comprises a flexible circuit having a flex circuit hub and a plurality of flex circuit branches integrally formed with and extending proximally from the flex circuit hub, the flexible circuit further including an outwardly-facing ablation electrode including an ablation electrode hub portion located on the flex circuit hub, and a plurality of ablation electrode branches integrally formed with the ablation electrode hub portion, each of the ablation electrode branches extending proximally along a portion of a respective one of the flex circuit branches and terminating in an ablation electrode proximal end.

20 Claims, 10 Drawing Sheets

(52) U.S. Cl.
CPC .............. *A61B 2018/00613* (2013.01); *A61B 2018/1417* (2013.01); *A61B 2018/1467* (2013.01)

(58) Field of Classification Search
CPC ........... A61B 2018/00613; A61B 2018/00875; A61B 2018/1417; A61B 2018/1467
See application file for complete search history.

(56)                    References Cited

U.S. PATENT DOCUMENTS

| | | | |
|---|---|---|---|
| 2012/0078077 A1* | 3/2012 | Harlev ................... | A61B 34/20 600/374 |
| 2015/0342491 A1* | 12/2015 | Marecki ............. | A61B 18/1492 600/374 |
| 2015/0374431 A1 | 12/2015 | Davies et al. | |
| 2017/0312007 A1* | 11/2017 | Harlev ............... | A61B 18/1482 |
| 2018/0168511 A1* | 6/2018 | Hall ................... | A61M 25/0074 |
| 2019/0216347 A1* | 7/2019 | Ghodrati ............. | A61B 5/6858 |
| 2019/0216503 A1 | 7/2019 | Otsubo | |
| 2022/0061911 A1 | 3/2022 | Howard et al. | |
| 2023/0079488 A1 | 3/2023 | Urbanski et al. | |

* cited by examiner

200

216D

216E

216F

214

264

216C

238

216B

216A

WIDE AREA FOCAL ABLATION CATHETER

CROSS REFERENCE TO RELATED APPLICATIONS

This application claims priority to and the benefit of U.S. Provisional Application No. 63/496,080, filed Apr. 14, 2023, which is incorporated by reference herein in its entirety.

TECHNICAL FIELD

The present disclosure relates to medical systems and methods for ablating tissue in a patient. More specifically, the present disclosure relates to medical systems and methods for ablation of tissue by electroporation.

BACKGROUND

Ablation procedures are used to treat many different conditions in patients. Ablation can be used to treat cardiac arrhythmias, benign tumors, cancerous tumors, and to control bleeding during surgery. Usually, ablation is accomplished through thermal ablation techniques including radiofrequency (RF) ablation and cryoablation. In RF ablation, a probe is inserted into the patient and radio frequency waves are transmitted through the probe to the surrounding tissue. The radio frequency waves generate heat, which destroys surrounding tissue and cauterizes blood vessels. In cryoablation, a hollow needle or cryoprobe is inserted into the patient and cold, thermally conductive fluid is circulated through the probe to freeze and kill the surrounding tissue. RF ablation and cryoablation techniques indiscriminately kill tissue through cell necrosis, which may damage or kill otherwise healthy tissue, such as tissue in the esophagus, phrenic nerve cells, and tissue in the coronary arteries.

Another ablation technique uses electroporation. In electroporation, or electro-permeabilization, an electrical field is applied to cells to increase the permeability of the cell membrane. The electroporation can be reversible or irreversible, depending on the strength of the electric field. If the electroporation is reversible, the increased permeability of the cell membrane can be used to introduce chemicals, drugs, and/or deoxyribonucleic acid (DNA) into the cell, prior to the cell healing and recovering. If the electroporation is irreversible, the affected cells are killed through apoptosis.

Irreversible electroporation can be used as a nonthermal ablation technique. In irreversible electroporation, trains of short, high voltage pulses are used to generate electric fields that are strong enough to kill cells through apoptosis. In ablation of cardiac tissue, irreversible electroporation can be a safe and effective alternative to the indiscriminate killing of thermal ablation techniques, such as RF ablation and cryoablation. Irreversible electroporation can be used to kill targeted tissue, such as myocardium tissue, by using an electric field strength and duration that kills the targeted tissue but does not permanently damage other cells or tissue, such as non-targeted myocardium tissue, red blood cells, vascular smooth muscle tissue, endothelium tissue, and nerve cells. There is a continuing need for improved devices and methods for performing cardiac tissue ablation through irreversible electroporation.

SUMMARY

In Example 1, a catheter for ablating cardiac tissue through irreversible electroporation, the catheter comprising a tubular outer shaft and an electrode assembly. The tubular outer shaft has a proximal end and an opposite distal end. The electrode assembly extends distally from the distal end of the outer shaft, and defines a distally located central hub portion and a plurality of splines each including a distal end portion extending proximally from the central hub portion, a proximal end portion attached to and constrained by the outer shaft, and an intermediate portion between the proximal end portion and the distal end portion. The electrode assembly further comprises a flexible circuit having a flex circuit hub and a plurality of flex circuit branches integrally formed with and extending proximally from the flex circuit hub, the flexible circuit further including an outwardly-facing ablation electrode including an ablation electrode hub portion located on the flex circuit hub, and a plurality of ablation electrode branches integrally formed with the ablation electrode hub portion, each of the ablation electrode branches extending proximally along a portion of a respective one of the flex circuit branches and terminating in an ablation electrode proximal end.

In Example 2, the catheter of example 1, wherein the flexible circuit further includes a plurality of spline sensing electrodes located on each flex circuit branch.

In Example 3, the catheter of example 2, wherein one or more of the spline sensing electrodes on each flex circuit branch are disposed within a periphery of the ablation electrode branch on the respective flex circuit branch and is electrically isolated from the ablation electrode.

In Example 4, the catheter of either of examples 2 or 3, wherein one or more of the plurality of spline sensing electrodes is located proximal to the proximal end of the ablation electrode branch on the respective flex circuit branch.

In Example 5, the catheter of any of examples 1-4, wherein the proximal end of each ablation electrode branch has a contoured shape.

In Example 6, the catheter of any of examples 1-5, wherein the distal end portion of each spline has a distal portion maximum width, and the intermediate portion of each spline has an intermediate portion maximum width that is greater than the distal portion maximum width.

In Example 7, the catheter of example 6, wherein the intermediate portion of each spline includes one or more scalloped regions each having a scalloped region width that is smaller than the intermediate portion maximum width.

In Example 8, the catheter of example 7, wherein at least one scalloped region is located in a portion of each spline on which a respective ablation electrode branch is located.

In Example 9, the catheter of any of examples 1-8, wherein each ablation electrode branch includes one or more ablation electrode branch apertures formed therein, and wherein one of the spline sensing electrodes is disposed within a respective one of the proximal ablation electrode branch apertures.

In Example 10, the catheter of example 9, wherein each ablation electrode branch aperture is bounded by a respective inner peripheral surface of the ablation electrode branch, and wherein an outer peripheral surface of the spline sensing electrode disposed within the respective ablation electrode branch aperture is spaced from the respective inner peripheral surface of the ablation electrode branch.

In Example 11, the catheter of any of examples 1-10, wherein the flex circuit further includes a hub sensing electrode centrally located on the flex circuit hub.

In Example 12, the catheter of any of examples 1-11, further comprising one or more shaft electrodes located proximate the distal end of the tubular outer shaft.

In Example 13, the catheter of example 12, wherein the ablation electrode and the one or more shaft electrodes are configured to define an anode/cathode electrode pair for delivery of electroporation ablation energy to target tissue.

In Example 14, the catheter of any of examples 1-13, wherein the electrode assembly further comprises a support member having a support member hub and a plurality of support member branches extending proximally from the support member hub, wherein the flex circuit hub is disposed over the support member hub, and each of the flex circuit branches is disposed over a respective one of the support member branches.

In Example 15, the catheter of example 14, wherein the electrode assembly includes a first region including an adhesive layer disposed between and mechanically attaching the flexible circuit to the support member, and a second region in which the flexible circuit and the support member are not directly mechanically attached together.

In Example 16, a catheter for ablating cardiac tissue through irreversible electroporation, the catheter comprising a tubular outer shaft and an electrode assembly. The tubular outer shaft has a proximal end and an opposite distal end. The electrode assembly extends distally from the distal end of the outer shaft, and defines a distally located central hub portion and a plurality of splines each including a distal end portion extending proximally from the central hub portion, a proximal end portion attached to and constrained by the outer shaft, and an intermediate portion between the proximal end portion and the distal end portion. The electrode assembly further comprises a support member and a flexible circuit. The support member has a support member hub and a plurality of support member branches extending proximally from the support member hub. The flexible circuit is disposed over an outer surface of the support member and has a flex circuit hub disposed over the support member hub, and a plurality of flex circuit branches, each of the flex circuit branches disposed over a respective one of the support member branches, the flexible circuit further including an ablation electrode including an ablation electrode hub portion located on the flex circuit hub, and a plurality of ablation electrode branches integrally formed with the ablation electrode hub portion, each of the ablation electrode branches extending proximally along a portion of a respective one of the flex circuit branches and terminating in an ablation electrode proximal end.

In Example 17, the catheter of example 16, wherein the flexible circuit further comprises a plurality of spline sensing electrodes located on each flex circuit branch, wherein one or more of the spline sensing electrodes on each flex circuit branch is disposed within a periphery of the respective ablation electrode branch disposed on the flex circuit branch and is electrically isolated from the ablation electrode.

In Example 18, the catheter of example 17, wherein the proximal end of each ablation electrode branch has a contoured shape.

In Example 19, the catheter of example 17, wherein one or more of the plurality of spline sensing electrodes is located proximal to the proximal end of the ablation electrode branch on the respective flex circuit branch.

In Example 20, the catheter of example 17, wherein each ablation electrode branch includes one or more ablation electrode branch apertures formed therein, and wherein one of the spline sensing electrodes is disposed within a respective one of the ablation electrode branch apertures.

In Example 21, the catheter of example 20, wherein each ablation electrode branch aperture is bounded by a respective inner peripheral surface of the ablation electrode branch, and wherein an outer peripheral surface of the spline sensing electrode disposed within the respective ablation electrode branch aperture is spaced from the respective inner peripheral surface of the ablation electrode branch.

In Example 22, the catheter of example 17, wherein the distal end portion of each spline has a distal portion maximum width, and the intermediate portion of each spline has an intermediate portion maximum width that is greater than the distal portion maximum width.

In Example 23, the catheter of example 22, wherein the intermediate portion of each spline includes one or more scalloped regions each having a scalloped region width that is smaller than the intermediate portion maximum width, and wherein at least one scalloped region is located in a portion of each spline on which a respective ablation electrode branch is located.

In Example 24, the catheter of example 17, wherein the flexible circuit further includes a hub sensing electrode centrally located on the flex circuit hub.

In Example 25, the catheter of example 17, further comprising one or more shaft electrodes located proximate the distal end of the tubular outer shaft.

In Example 26, the catheter of example 25, wherein the ablation electrode and the one or more shaft electrodes are configured to define an anode/cathode electrode pair for delivery of electroporation ablation energy to target tissue.

In Example 27, a catheter for ablating cardiac tissue through irreversible electroporation, the catheter comprising a tubular outer shaft and an electrode assembly. The tubular outer shaft has a proximal end and an opposite distal end. The electrode assembly extends distally from the distal end of the outer shaft, and defines a distally-located central hub portion and a plurality of splines each including a distal end portion extending proximally from the central hub portion, a proximal end portion attached to and constrained by the outer shaft, and an intermediate portion between the proximal end portion and the distal end portion. The electrode assembly further comprises a support member and a flexible circuit. The support member is formed from a superelastic material and has a support member hub and a plurality of support member branches integrally formed with and extending proximally from the support member hub. The flexible circuit is disposed over an outer surface of the support member and has a flex circuit hub disposed over the support member hub, and a plurality of flex circuit branches integrally formed with the flex circuit hub, each of the flex circuit branches disposed over a respective one of the support member branches. The flexible circuit further includes an ablation electrode including an ablation electrode hub portion located on the flex circuit hub, and a plurality of ablation electrode branches integrally formed with the ablation electrode hub portion, each of the ablation electrode branches extending proximally along a portion of a respective one of the flex circuit branches, a plurality of spline sensing electrodes, wherein one or more of the spline sensing electrodes is disposed within a periphery of each of the ablation electrode branches and is electrically isolated from the ablation electrode.

In Example 28, the catheter of example 27, wherein the distal end portion of each spline has a distal portion maximum width, and the intermediate portion of each spline has an intermediate portion maximum width that is greater than the distal portion maximum width.

In Example 29, the catheter of example 28, wherein the intermediate portion of each spline includes one or more scalloped regions each having a scalloped region width that is smaller than the intermediate portion maximum width, and wherein at least one scalloped region is located in a portion of each spline on which a respective ablation electrode branch is located.

In Example 30, the catheter of example 29, wherein one or more of the plurality of spline sensing electrodes is located proximal to the proximal end of the ablation electrode branch on the respective flex circuit branch.

In Example 31, the catheter of example 30, wherein the flexible circuit further includes a hub sensing electrode centrally located on the flex circuit hub.

In Example 32, a catheter for ablating cardiac tissue through irreversible electroporation, the catheter comprising a tubular outer shaft and an electrode assembly. The tubular outer shaft has a proximal end and an opposite distal end. The electrode assembly extends distally from the distal end of the outer shaft, and comprises a flexible circuit having a distally located central flex circuit hub and a plurality of flex circuit branches extending proximally from the hub portion, each of the flex circuit branches defining, at least in part, an electrode assembly spline and including a proximal end portion attached to and constrained by the outer shaft. The flexible circuit further includes an ablation electrode including an ablation electrode hub portion located on the flex circuit hub, and a plurality of ablation electrode branches integrally formed with the ablation electrode hub portion, each of the ablation electrode branches extending proximally along a portion of a respective one of the flex circuit branches and terminating in a proximal end.

In Example 33, the catheter of example 32, wherein the flexible circuit further comprises a plurality of spline sensing electrodes located on each flex circuit branch, wherein one or more of the plurality of spline sensing electrodes on each flex circuit branch is disposed within a periphery of the respective ablation electrode branch on the flex circuit branch and is electrically isolated from the ablation electrode.

In Example 34, the catheter of example 33, wherein one or more of the plurality of spline sensing electrodes is located proximal to the proximal end of the ablation electrode branch on each respective flex circuit branch.

In Example 35, the catheter of example 34, wherein the flexible circuit further comprises a hub sensing electrode centrally located on the flex circuit hub.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
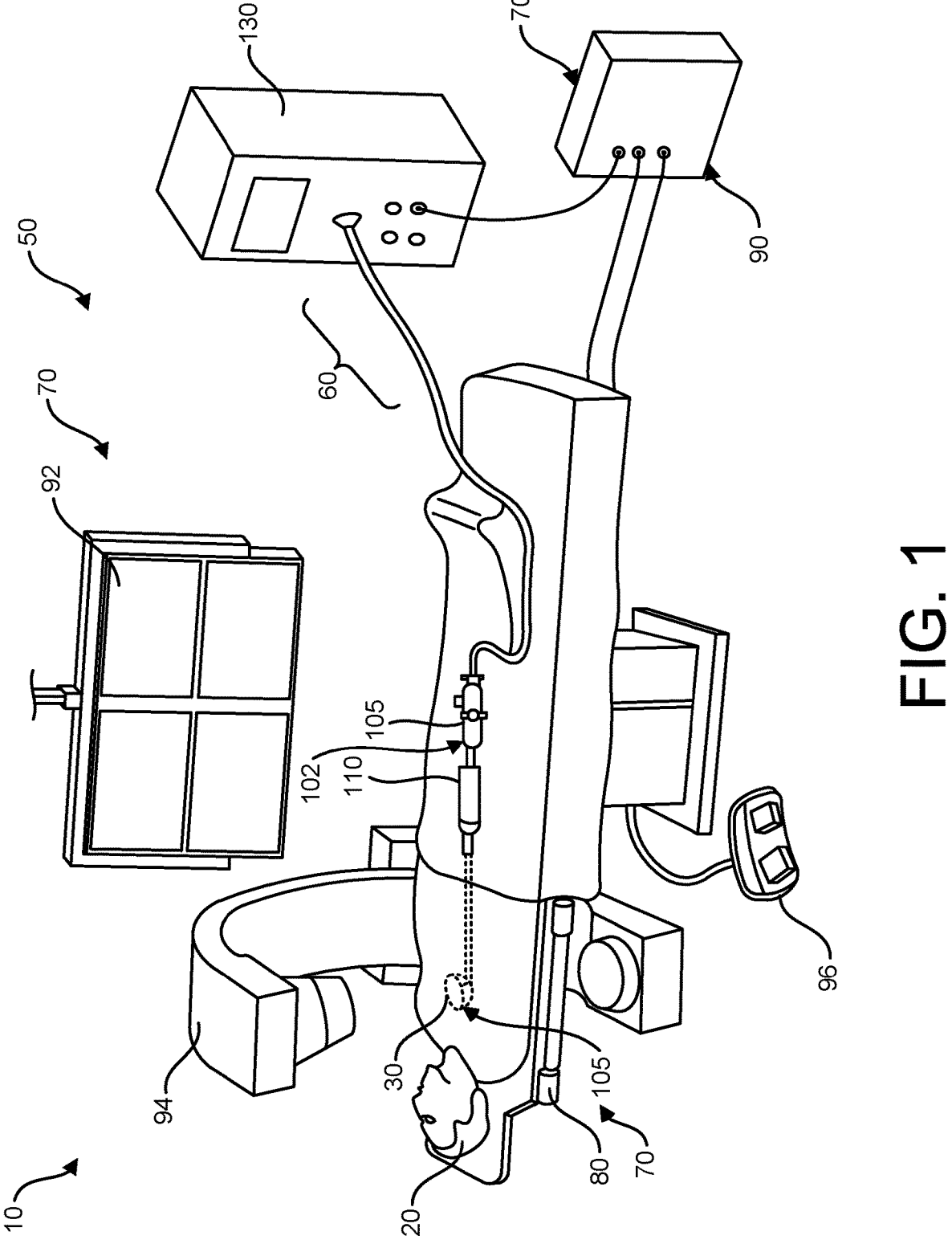
FIG. 1 is a diagram illustrating an exemplary clinical setting for treating a patient, and for treating a heart of the patient, using an electrophysiology system, in accordance with embodiments of the subject matter of the disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

For purposes of promoting an understanding of the principles of the present disclosure, reference is now made to the examples illustrated in the drawings, which are described below. The illustrated examples disclosed herein are not intended to be exhaustive or to limit the disclosure to the precise form disclosed in the following detailed description. Rather, these exemplary embodiments were chosen and described so that others skilled in the art may use their teachings. It is not beyond the scope of this disclosure to have a number (e.g., all) the features in a given example used across all examples. Thus, no one figure should be interpreted as having any dependency or requirement related to any single component or combination of components illustrated therein. Additionally, various components depicted in a given figure may be, in examples, integrated with various ones of the other components depicted therein (and/or components not illustrated), all of which are considered to be within the ambit of the present disclosure.

The terms "couples," "coupled," "connected," "attached," and the like along with variations thereof are used to include both arrangements wherein two or more components are in direct physical contact and arrangements wherein the two or more components are not in direct contact with each other (e.g., the components are "coupled" via at least a third component), but yet still cooperate or interact with each other.

Throughout the present disclosure and in the claims, numeric terminology, such as first and second, is used in reference to various components or features. Such use is not intended to denote an ordering of the components or features. Rather, numeric terminology is used to assist the reader in identifying the component or features being referenced and should not be narrowly interpreted as providing a specific order of components or features.

FIG. 1 is a diagram illustrating an exemplary clinical setting 10 for treating a patient 20, and for treating a heart 30 of the patient 20, using an electrophysiology system 50, in accordance with embodiments of the subject matter of the disclosure. The electrophysiology system 50 includes an electroporation catheter system 60 and an electro-anatomical mapping (EAM) system 70, which includes a localization field generator 80, a mapping and navigation controller 90, and a display 92. Also, the clinical setting 10 includes additional equipment such as imaging equipment 94 (represented by the C-arm) and various controller elements, such as a foot controller 96, configured to allow an operator to control various aspects of the electrophysiology system 50. As will be appreciated by the skilled artisan, the clinical setting 10 may have other components and arrangements of components that are not shown in FIG. 1.

The electroporation catheter system 60 includes an electroporation catheter 100 having a proximal portion 102 and a distal portion 105, an introducer sheath 110, and an electroporation console 130. Additionally, the electroporation catheter system 60 includes various connecting elements, e.g., cables, umbilicals, and the like, that operate to functionally connect the components of the electroporation catheter system 60 to one another and to the components of the EAM system 70. This arrangement of connecting elements is not of critical importance to the present disclosure, and the skilled artisan will recognize that the various components described herein can be interconnected in a variety of ways.

In embodiments, the introducer sheath 110 is operable to provide a delivery conduit through which the electroporation catheter 100, in particular all or part of the distal portion 105 thereof, can be deployed to the specific target sites within the patient's heart 30.

In embodiments, the electroporation catheter system 60 is configured to deliver electric field energy to targeted tissue in the patient's heart 30 to create tissue apoptosis, rendering the tissue incapable of conducting electrical signals.

The electroporation console 130 is configured to control functional aspects of the electroporation catheter system 60. In embodiments, the electroporation console 130 includes one or more controllers, microprocessors, and/or computers that execute code out of memory to control and/or perform the functional aspects of the electroporation catheter system 60. In embodiments, the memory can be part of the one or more controllers, microprocessors, and/or computers, and/or part of memory capacity accessible through a network, such as the world wide web. In embodiments, the electroporation console 130 includes pulse generator hardware, software and/or firmware configure to generate electrical pulses in predefined waveforms, which are transmitted to electrodes on the electroporation catheter 100 to generate electric fields sufficient to achieve the desired clinical effect, in particular ablation of target tissue through irreversible electroporation. In embodiments, the electroporation console 130 can deliver the pulsed waveforms to the electroporation catheter 100 in a monopolar or bipolar mode of operation, as will be described in further detail herein.

The EAM system 70 is operable to track the location of the various functional components of the electroporation catheter system 60, and to generate high-fidelity three-dimensional anatomical and electro-anatomical maps of the cardiac chambers of interest. In embodiments, the EAM system 70 can be the RHYTHMIA™ HDx mapping system marketed by Boston Scientific Corporation. Also, in embodiments, the mapping and navigation controller 90 of the EAM system 70 includes one or more controllers, microprocessors, and/or computers that execute code out of memory to control and/or perform functional aspects of the EAM system 70, where the memory, in embodiments, can be part of the one or more controllers, microprocessors, and/or computers, and/or part of memory capacity accessible through a network, such as the world wide web.

As will be appreciated by the skilled artisan, the depiction of the electrophysiology system 50 shown in FIG. 1 is intended to provide a general overview of the various components of the system 50 and is not in any way intended to imply that the disclosure is limited to any set of components or arrangement of the components. For example, the skilled artisan will readily recognize that additional hardware components, e.g., breakout boxes, workstations, and the like, can and likely will be included in the electrophysiology system 50.

The EAM system 70 generates a localization field, via the field generator 80, to define a localization volume about the heart 30, and one or more location sensors or sensing elements on the tracked device(s), e.g., the electroporation catheter 100, generate an output that can be processed by the mapping and navigation controller 90 to track the location of the sensor, and consequently, the corresponding device, within the localization volume. In the illustrated embodiment, the device tracking is accomplished using magnetic tracking techniques, whereby the field generator 80 is a magnetic field generator that generates a magnetic field defining the localization volume, and the location sensors on the tracked devices are magnetic field sensors.

In other embodiments, impedance tracking methodologies may be employed to track the locations of the various devices. In such embodiments, the localization field is an electric field generated, for example, by an external field generator arrangement, e.g., surface electrodes, by intra-body or intra-cardiac devices, e.g., an intracardiac catheter, or both. In these embodiments, the location sensing elements can constitute electrodes on the tracked devices that generate outputs received and processed by the mapping and navigation controller 90 to track the location of the various location sensing electrodes within the localization volume.

In embodiments, the EAM system 70 is equipped for both magnetic and impedance tracking capabilities. In such embodiments, impedance tracking accuracy can, in some instances be enhanced by first creating a map of the electric field induced by the electric field generator within the cardiac chamber of interest using a probe equipped with a magnetic location sensor, as is possible using the aforementioned RHYTHMIA HDx™ mapping system. One exemplary probe is the INTELLAMAP ORION™ mapping catheter marketed by Boston Scientific Corporation.

Regardless of the tracking methodology employed, the EAM system 70 utilizes the location information for the various tracked devices, along with cardiac electrical activity acquired by, for example, the electroporation catheter 100 or another catheter or probe equipped with sensing electrodes, to generate, and display via the display 92, detailed three-dimensional geometric anatomical maps or representations of the cardiac chambers as well as electro-anatomical maps in which cardiac electrical activity of interest is superimposed on the geometric anatomical maps. Furthermore, the EAM system 70 can generate a graphical representation of the various tracked devices within the geometric anatomical map and/or the electro-anatomical map.

Embodiments of the present disclosure provide systems, devices, and methods for selective and rapid application of pulsed electric fields to ablate tissue by irreversible electroporation. Generally, the systems, devices, and methods described herein may be used to generate large electric field magnitudes at desired regions of interest and reduce peak electric field values elsewhere in order to reduce unnecessary tissue damage and electrical arcing. An irreversible electroporation system as described herein may include a signal generator and a processor configured to apply one or more voltage pulse waveforms to a selected set of electrodes of an ablation device to deliver energy to a region of interest (e.g., ablation energy for a set of tissue in a pulmonary vein ostium or antrum). The pulse waveforms disclosed herein may aid in therapeutic treatment of a variety of cardiac arrhythmias (e.g., atrial fibrillation). In order to deliver the pulse waveforms generated by the signal generator, one or more electrodes of the ablation device may have an insulated electrical lead configured for sustaining a voltage potential in the order of several hundred volts to several thousand volts. The electrodes may be independently addressable such that each electrode may be controlled (e.g., deliver energy) independently of any other electrode of the device. In this manner, the electrodes may deliver different energy waveforms with different timing synergistically for electroporation of tissue.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may comprise one or more of the methods, systems, and devices described in International Application Serial No. PCT/US2016/057664, filed on Oct. 19, 2016, and titled "SYSTEMS, APPARATUSES AND METHODS FOR DELIVERY OF ABLATIVE ENERGY TO TISSUE," the contents of which are hereby incorporated by reference in its entirety.

Figure 2A:
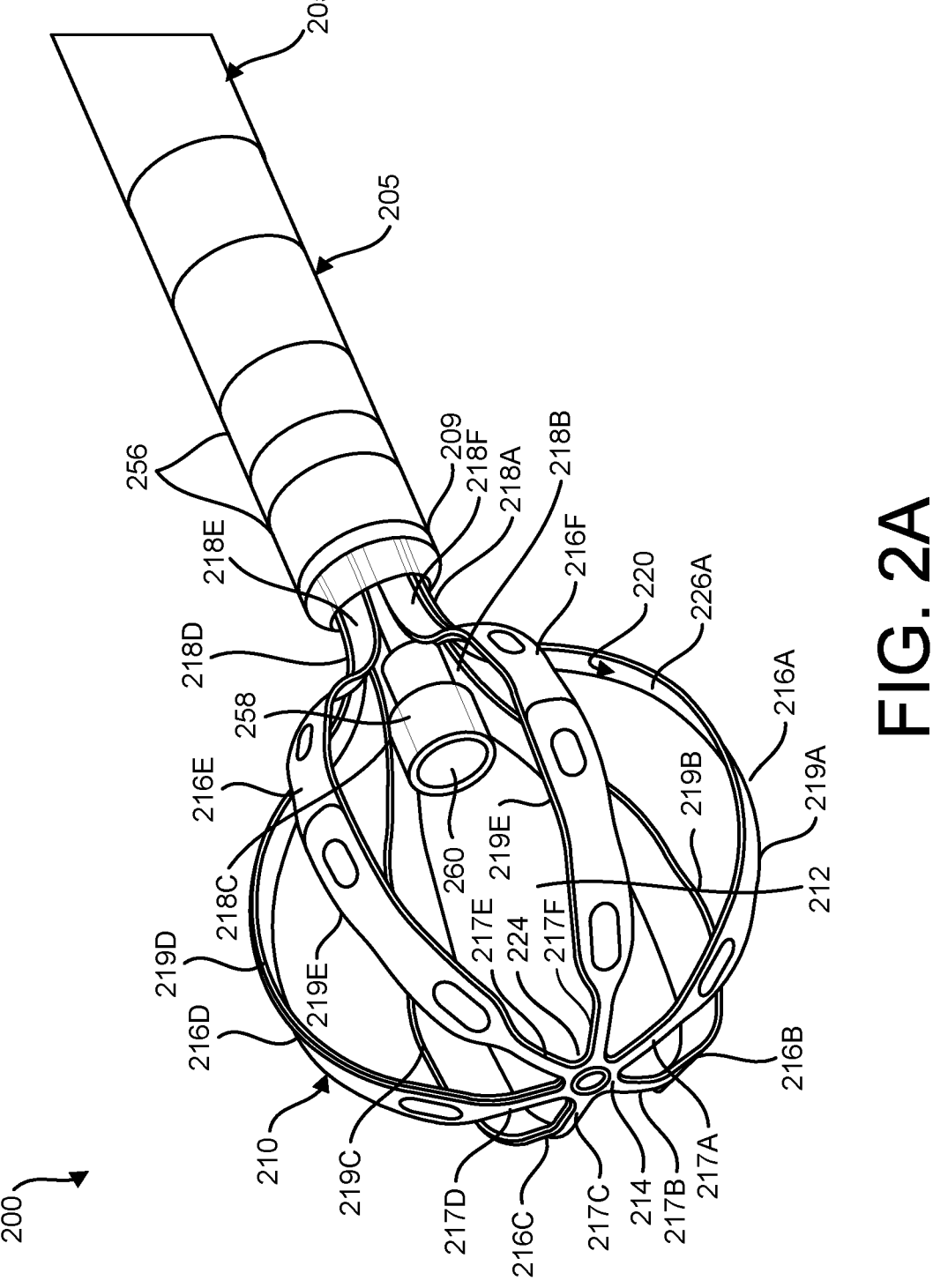
FIGS. 2A and 2B are perspective and end view illustrations, respectively, of a distal portion of a splined catheter for use in the electrophysiology system of FIG. 1, in accordance with embodiments of the subject matter of the disclosure.
Figure 2B:
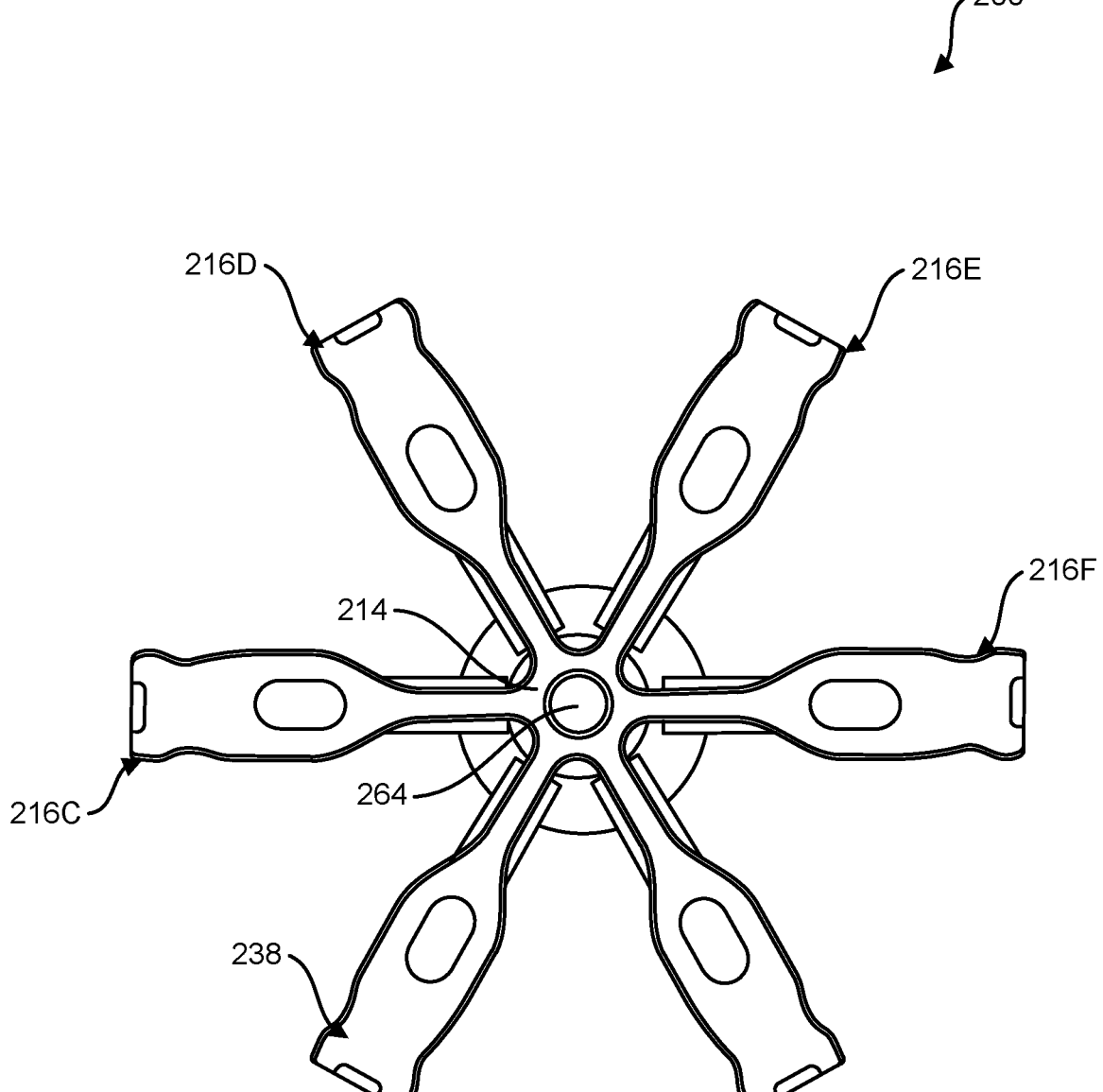

FIGS. 2A and 2B are partial perspective and end view illustrations, respectively, of an electroporation catheter 200 having a catheter distal portion 205 according to an embodiment of the present disclosure. The electroporation catheter 200 corresponds to the electroporation catheter 100 described with respect to FIG. 1. The electroporation catheter 200 has a tubular outer shaft 202 having a shaft distal end 209, and an electrode assembly 210 extending distally from the distal end 209 of the outer shaft 202. In embodiments, the electrode assembly 210 is configured to self-expand from a collapsed configuration when constrained within a delivery sheath to a pre-defined expanded configuration defining an inner space 212. As will be explained in greater detail herein, the electrode assembly 210 comprises an ablation electrode configured to receive pulsed electrical signals/waveforms from the electroporation console 130 (FIG. 1), thereby creating pulsed electric fields sufficient for ablating target tissue via irreversible electroporation. Additionally, the electrode assembly 210 further includes a plurality of mapping and sensing electrodes configured for, among other things, sensing cardiac electrical signals, localization of the electrode assembly 210 within the patient anatomy (e.g., via the EAM system 70 of FIG. 1), and determining proximity to target tissue within the anatomy.

Overall, the electrode assembly 210 and other electrode assembly embodiments described herein within the scope of the present disclosure, is primarily designed for the creation of relatively localized ablation lesions (i.e., focal lesions), as compared to relatively large diameter circumferential lesions created in pulmonary vein isolation procedures. However, the skilled artisan will appreciate that the teachings of the present disclosure can be readily adapted for a catheter capable of large diameter circumferential lesions. The designs of the various electrode assembly embodiments described herein can provide the clinician with a wide range of capabilities for monopolar and bipolar focal pulsed field ablation of cardiac tissue, combined with the ability to perform localized (i.e., at the location of the delivery of pulsed field ablative energy), high fidelity sensing of cardiac tissue, e.g., for lesion or conduction block assessment, tissue contact determinations, and the like.

Figure 2C:
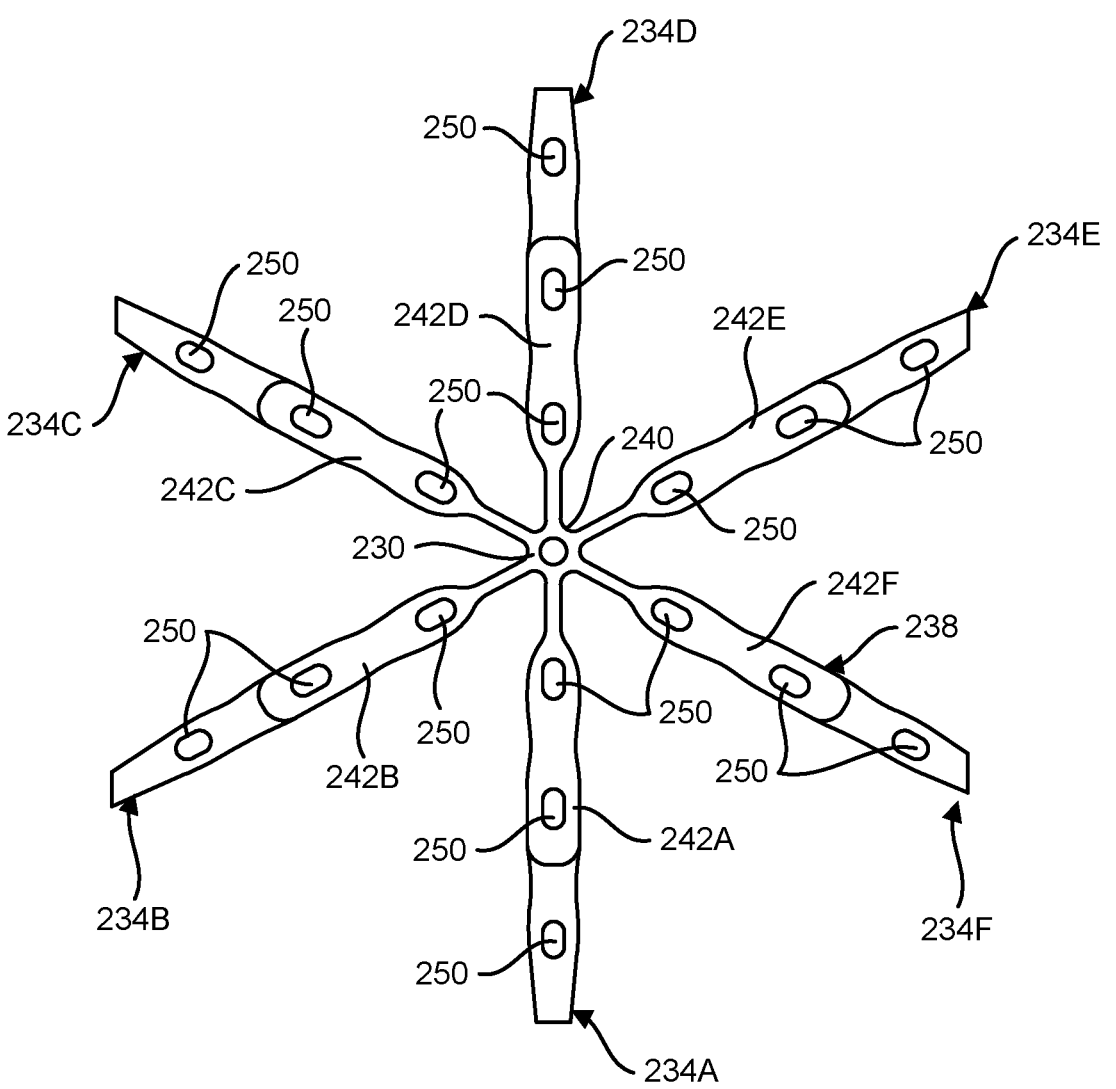
FIG. 2C is a partial plan view of an electrode assembly of the splined catheter shown in two-dimensions, in accordance with embodiments of the subject matter of the disclosure.

FIG. 2C is a partial plan view of the electrode assembly 210 of the electroporation catheter 200 shown, shown in two-dimensions to illustrate the layout of the electrode assembly 210. Referring to FIGS. 2A-2C together, in the illustrated embodiment, the electrode assembly 210 as a whole has a distally-located central hub portion 214 and a plurality of splines 216A-216F extending proximally from the central hub portion 214. As further shown, each respective spline 216A-216F has a distal end portion 217A-217F, a proximal end portion 218A-218F, and an intermediate portion 219A-219F extending between the distal end portion 217A-217F and the proximal end portion 218A-218F. As shown, each of the proximal end portions 218A-218F is attached to and constrained by the distal end 209 of the outer shaft 202. As further shown, in the illustrated embodiment, the intermediate portion 219A-219F of each spline 216A-216F has a lateral width that is greater than the lateral width of each of the respective distal end portions 217A-217F. In embodiments, the particular geometry of the splines 216A-216F and the related components, e.g., ablation and mapping electrodes, is optimized to provide desired mechanical and therapeutic/diagnostic capabilities.

In the illustrated embodiment, the splines 216A-216F are composed of a support member 220 and a flexible circuit 222 secured to and disposed over an outer surface of the support member 220. The support member 220 functions, among other things, as a primary structural support of the electrode assembly 210, and thus primarily defines the mechanical characteristics of the electrode assembly 210. In embodiments, the support member 220 is formed from a superelastic material (metal or polymer) to provide desired mechanical/structural properties to the electrode assembly 210. In embodiments, the support member 220 is formed from a superelastic metal alloy, e.g., a nickel-titanium alloy.

The support member 220 includes a support member hub 224 and a plurality of support member branches (for ease of illustration, only support member branch 226A is labeled in FIG. 2A). In embodiments, the support member branches are integrally formed with and extend proximally from the support member hub 224. For example, the entire support member 200 may be cut from a single sheet of material using conventional manufacturing techniques. This unitary structure provides robust structural properties, for example, selective flexibility and enhanced fatigue characteristics, particularly in areas that are subject to relatively high stresses during manufacture and use of the electroporation catheter 200. Forming the support member 220 from a superelastic material such as a nickel-titanium alloy facilitates configuring the support member 220 to assume its desired unconstrained shape such as shown in FIG. 2A due to the shape memory properties of the material, while providing sufficient flexibility necessary to collapse the electrode assembly 210 within a delivery sheath. In embodiments, the support member branches can be selectively configured along their lengths to tune the mechanical characteristics of the electrode assembly 210.

The flexible circuit 222 includes a flex circuit hub 230 and a plurality of flex circuit branches 234A-234F. In embodiments, the flex circuit hub 230 is disposed over and secured to the support member hub 224. In embodiments, the flex circuit branches 234A-234F are integrally formed with the flex circuit hub 230, and each of the flex circuit branches 234A-234F is disposed over and secured to a respective one of the support member branches. The flexible circuit 222 comprises a layered construction including one or more dielectric substrate layers, and conductive traces formed thereon. Similar to the support member 220, the unitary construction of the flexible circuit 222 enhances its structural properties, for example, by minimizing joints or other discontinuities at regions subject to relatively high stresses during use.

As shown, the flexible circuit 222 includes an ablation electrode 238 that has an ablation electrode hub portion 240 and a plurality of ablation electrode branches 242A-242F. In the illustrated embodiment, the distal ablation electrode hub portion 240 is located on the flex circuit hub 230. Additionally, the ablation electrode branches 242A-242F are integrally formed with the ablation electrode hub portion 240. Each of the ablation electrode branches 242A-242F extends proximally along a portion of a respective one of the flex circuit branches 234A-234F.

As further shown, the flexible circuit 222 includes a plurality of spline sensing electrodes 250. In the illustrated embodiment, two of the spline sensing electrodes 250 are disposed within a periphery of each of the ablation electrode branches 242A-242F, and one of the spline sensing electrodes 250 is located proximal to each of the ablation electrode branches 242A-242F on a respective flex circuit branch 234A-234F. The illustrated configuration is exemplary only, and other embodiments of the catheter 200 may have alternative configurations. Thus, in various embodiments, one or more of the spline sensing electrodes 250 may be disposed within the periphery of one or more of the ablation electrode branches 242A-242F and electrically isolated therefrom, and one or more of the spline sensing electrodes 250 may be located proximal to the ablation electrode branches 242A-242F on the respective flex circuit branch 234A-234F. In still other embodiments, no spline sensing electrodes 250 may be located outside the peripheries of the ablation electrode branches 242A-242F.

In some embodiments, the structural functionality of the support member 220 can be provided by a suitably designed flexible circuit 222. As such, although the electrode assembly 210 is described in detail as including the support member 220 as a primary structural member, in other embodiments the support member 220 can be omitted in its entirety and the corresponding functionality can be provided by the flexible circuit 222.

In the particular illustrated embodiment, the electroporation catheter 200 includes a pair of shaft electrodes 256 located proximate the distal end 209 of the outer shaft 202, as well as a central post 258 extending distally from the distal end 209 of the outer shaft 202. As shown, the central post 258 extends partially into the inner space 212, and includes a post electrode 260. In embodiments, the central post 258 may house additional components. For example, in embodiments, a magnetic navigation sensor (not shown)

may be partially or wholly disposed within the central post 258. However, in other embodiments such a sensor may be located elsewhere on the electroporation catheter 200 (e.g., within the outer shaft 202). In the illustrated embodiment, the electrode assembly 210 further includes a hub sensing electrode 264 centrally located on the flex circuit hub 230.

In embodiments, one or both of the shaft electrodes 256 can be configured to be paired with the ablation electrode 238 to form an anode/cathode ablation electrode pair for generation of an ablative electric field in a bipolar mode. In embodiments, the shaft electrodes 256 may have additional functions, e.g., and without limitation, as additional sensing electrodes for sensing cardiac electrical signals, and for use as localization sensors for impedance tracking of the electrode assembly 210.

The post electrode 260 can provide a number of functional advantages. In one example, the post electrode 260 can operate as a reference for unipolar electrograms, in lieu of reliance on surface ECG patch electrodes as are otherwise known in the art. The location of the post electrode 260 for this purpose positions the reference electrode much closer to the tissue being sensed than is possible with the conventional surface ECG approach, which may advantageously minimize far field noise and provide much sharper unipolar electrograms than what are possible using surface ECG electrodes. The post electrode 260 may also be operable to sense and measure other electrical parameters, e.g., voltages between it and the ablation electrodes or other sensing electrodes on the electrode assembly 210, thereby providing data usable for, in some examples, determining the shape of the electrode assembly during use (including when deformed by forces applied by cardiac walls), and displaying shape information via the EAM system 70 (FIG. 1).

In embodiments, the hub sensing electrode 264 allows tissue surface mapping to be conducted in a "forward" manner, eliminating the need to manipulate the electrode assembly 210 to place the spline sensing electrodes 250 against or proximate the tissue to be mapped. The inclusion of the hub sensing electrodes 264 further enhances bipolar sensing capabilities by providing for, in the illustrated embodiment, six additional bi-poles when paired with any of the distal-most spline sensing electrodes 250.

Figures 2D, 2E:
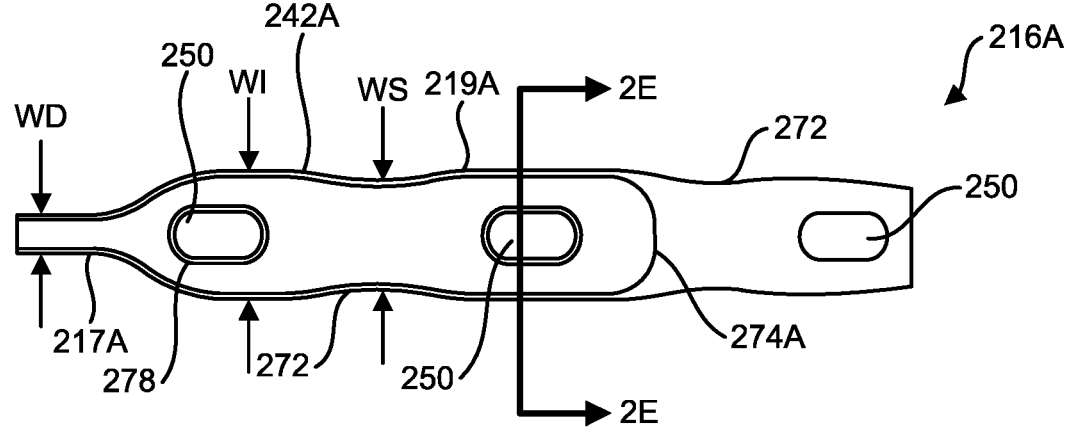
FIG. 2D is an enlarged plan view of a portion of a spline of the electrode assembly shown in FIGS. 2A-2C, in accordance with embodiments of the subject matter of the disclosure.
FIG. 2E is a schematic cross-sectional view of a portion of a spline of the electrode assembly of FIGS. 2A-2C, in accordance with embodiments of the subject matter of the disclosure.

FIG. 2D is an enlarged plan view of a portion of the spline 216A, the ablation electrode branch 242A, and the flex circuit branch 234A, according to embodiments of the present disclosure. The structural features illustrated in FIG. 2D are representative the splines 216A-216F, the ablation electrode branches 242A-242F and the flex circuit branches 234A-234F.

As shown, the distal end portion 217A of the spline 216A has a maximum width $W_D$, and the intermediate portion 219A of the spline 216A has a maximum width $W_I$ that is greater than the maximum width $W_D$ of the distal end portion. In the particular embodiment shown, the intermediate portion 219A further includes one or more scalloped regions 272 wherein the opposing outer edges of the spline 216A have a concave shape. In embodiments, the scalloped regions 272 are selectively located along the length of the spline 216A and each have a scalloped region minimum width $W_S$ that is less than the maximum width $W_I$ of the intermediate portion 219A. When present, the scalloped regions 272 affect the mechanical properties (e.g., bending flexibility) of the spline 216A, to, for example, facilitate deformation of the spline 216A when it is in contact with target tissue, as well as facilitating collapse of the electrode assembly 210 when it is retracted into a delivery sheath. However, in some embodiments, the scalloped regions 272 are omitted, and the spline 216A has a generally linear shape along the intermediate portion 219A. In the illustrated embodiment, at least one of the scalloped regions 272 is located in the region of the spline 216A on which a portion of the ablation electrode branch 242A is disposed, and between the spline sensing electrodes 250 located thereon.

As shown, the ablation electrode branch 242A has a proximal end 274A. In the illustrated embodiment, the proximal end 274A is contoured and shaped to enhance electric field generation and clinical efficacy when the catheter 200 is configured to operate in bi-polar energy delivery mode, with the ablation electrode 238 and one or both of the shaft electrodes 256 paired as a bi-polar electrode pair. In other embodiments, however, the proximal end 274A can take on different shapes, e.g., semi-circular. The location of the proximal end 274A (which as will be appreciated, defines the length of the ablation electrode branch 242A and consequently defines, in part, the overall surface area of the ablation electrode 238) can be varied from embodiment to embodiment depending on the particular clinical needs required of the catheter 200.

As further shown, the ablation electrode branch 242A includes a plurality of ablation electrode branch apertures 278, and one of the spline sensing electrodes 250 is disposed within each of the ablation electrode branch apertures 278.

FIG. 2E is a schematic cross-sectional view of the spline 216A taken alone the line 2E-2E in FIG. 2D, illustrating an exemplary configuration of the spline 216A, the flex circuit branch 234A and the ablation electrode branch 242A in the intermediate portion 219A. As illustrated in FIG. 2E, the spline 216A includes the support member branch 226A and the flex circuit branch 234A is disposed thereon. As further shown, the flex circuit branch 234A comprises a layered structure that, except as specifically distinguished herein, may be typical of flexible circuits for use in medical device electrode assemblies. In the particular embodiment illustrated in FIG. 2E, the flex circuit branch 234A includes a dielectric base layer 280A disposed over the support member branch 226A, an optional inner flexible adhesive layer 282A over the base layer 280A, a conductive trace layer 284A over the adhesive layer 282A (when present), and a dielectric upper layer 286A over the conductive trace layer 284A. The dielectric materials chosen for the layers 280A and 286A can be any conventional materials suitable for use in flexible circuits for medical devices, e.g., polyamides. It is emphasized that the present disclosure is not limited to the particular flex circuit stacking arrangement illustrated in FIG. 2E, and that the skilled artisan will readily understand alternative arrangements that may be utilized.

As further shown in FIG. 2E, the ablation electrode branch 242A and the spline sensing electrode 250 are disposed over the upper layer 286A. In embodiments, the electrodes 242A and 250 may have a coating of a suitable biocompatible metal, e.g., gold. In embodiments, the outer surfaces of the electrodes 242A and 250 may be treated to provide the electrical properties desired for the particular clinical application.

As illustrated in FIG. 2E, the ablation electrode branch aperture 278 is bounded by an inner peripheral surface 288 of the ablation electrode branch 242A, and an outer peripheral surface 290 of the spline sensing electrode 250 is spaced from the inner peripheral surface 288 of the ablation electrode branch 242A by a gap G. Conventionally, the skilled artisan would expect to dispose a dielectric material between the outer peripheral surface 290 and the inner peripheral surface 288 of the ablation electrode branch 242A so as to minimize potential undesirable effects, e.g., bubble formation due to arcing or edge effects at the periphery of the ablation electrode branch 242A, that may result when the pulsed waveform is delivered to the ablation electrode branch 242A. However, the inventors of the present disclosure found that the propensity for bubble formation within the blood pool when the gap G is present is effectively the same as in an arrangement where a dielectric material is disposed in this region. These advantageous results can be enhanced by selectively tailoring the dimension of the gap G. In embodiments, the gap G can range from about 0.050 millimeters to about 0.50 millimeters. In one embodiment, the gap G is about 0.50 millimeters.

In the embodiments described and illustrated herein, each of the ablation assemblies has six splines. It is emphasized, however, that this is for illustration purposes, and thus the skilled artisan will readily recognize that for a given clinical application more or fewer than six splines may be included.

Figure 3A:
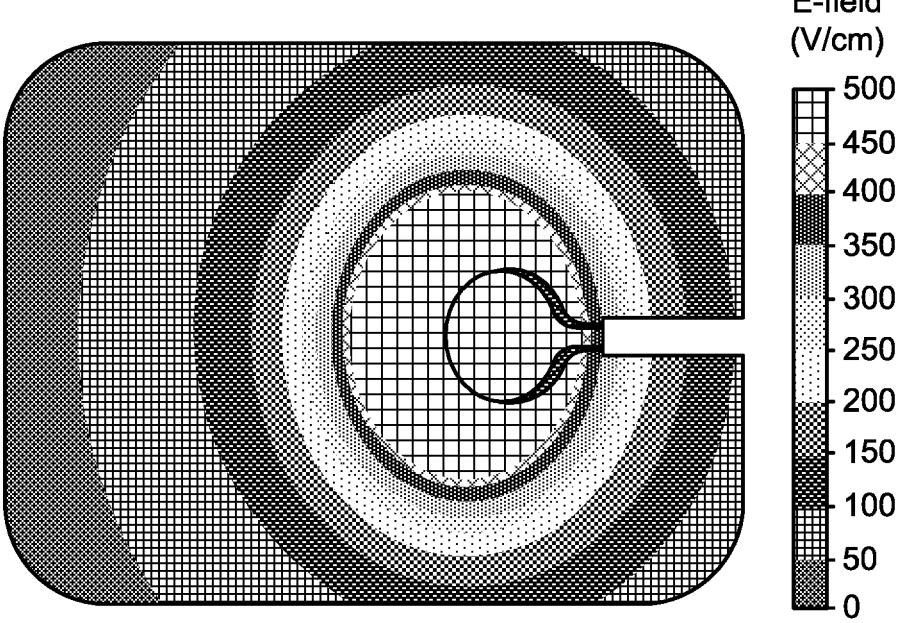
FIGS. 3A and 3B are schematic illustrations of exemplary electric fields generated using the electrode assembly illustrated in FIGS. 2A-2D, in accordance with embodiments of the subject matter of the disclosure.

In the various embodiments, each of the ablation electrode 238, the spline sensing electrodes 250, the shaft electrodes 256 and the hub sensing electrode 264 are separately electrically connected to the control system of the electroporation console 130 (FIG. 1) and are individually addressable to provide for a wide range of ablation and sensing modes, e.g., monopolar and bipolar modes. During monopolar ablation operation, the ablation electrode 238 and an electrode located elsewhere (e.g., a dispersive electrode located on the patient, typically on the back, buttocks, or other suitable anatomical location, or an electrode on a different catheter or probe located outside the cardiac chamber in which the electrode assembly 210 is located) is configured to operate at the opposite polarity. In one example, the ablation electrode 238 is configured as an anode or cathode, and an extracorporeal dispersive electrode located on a back patch is configured as the other of the cathode or anode. The skilled artisan will readily recognize a wide range of monopolar ablation electrode configurations that may be utilized. In monopolar mode, the corresponding electric field generated about the ablation electrode 238 has a generally semi-spherical shape, as depicted in the exemplary E-field profile shown in FIG. 3A.

Figure 3B:
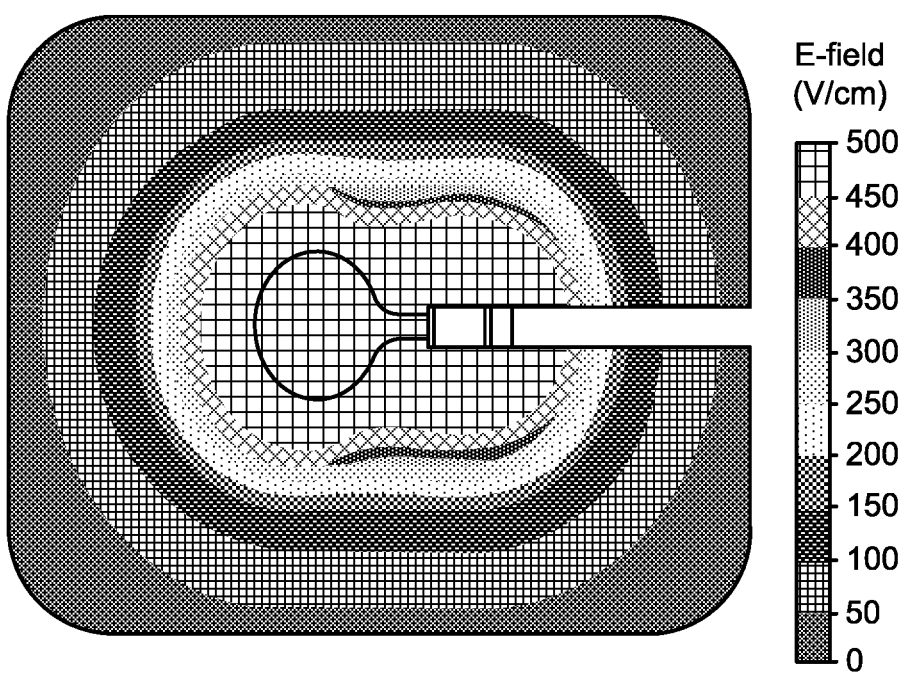

During bipolar ablation operation, the ablation electrode 238 is configured as the anode (or cathode) and one or both of the shaft electrodes 256 is configured as the cathode (or anode). The resulting electric field generated in the aforementioned bipolar mode tends to have a three-dimensional hourglass profile, as depicted in FIG. 3B.

As will be appreciated by the skilled artisan, any of the spline sensing electrodes 250, the shaft electrodes 256, the post reference electrode 260 or the hub sensing electrode 264 can also be individually addressed for bipolar sensing and mapping an any number of combinations. Additionally, in embodiments, the aforementioned individual addressability allows any of the spline sensing electrodes and/or the hub sensing electrode 264 to be configured by the control system as ablation electrodes to operate in conjunction with the ablation electrode 238, in either monopolar or bipolar mode.

Referring again to FIGS. 2A-2E together, in embodiments, the geometries and locations of the spline sensing electrodes 250 and the hub sensing electrode 264 are configured to provide a wide range of high-fidelity sensing and mapping capabilities. In the illustrated embodiments, the spline sensing electrodes 250 are each depicted as having a generally obround geometry, although in other embodiments they may have different geometries, e.g., circular, semi-circular, elliptical, and the like). In embodiments, the spline sensing electrodes 250 may be uniformly spaced along the length of the respective spline 216A. In the embodiment shown, the distal-most spline electrodes 250 and the hub sensing electrode 264 are more closely spaced together than, for example, the spline sensing electrodes 250 are from one another along a respective spline. Similarly, the spacing between the distal-most spline sensing electrodes 250 on adjacent splines is smaller than the spacing of the more proximally-located spline sensing electrodes 250 on adjacent splines. Accordingly, the distal-most spline sensing electrodes 250 can be utilized to form relatively tight bi-poles when paired with the hub sensing electrode 264 or a corresponding distal-most spline sensing electrode on an adjacent spline, thus providing for very high-fidelity, localized sensing of cardiac electrical activity.

Overall, the design and construction of the electrode assembly 210 is particularly suited for creation of effective wide-area focal ablation lesions via pulsed field ablative energy, both in monopolar and bipolar modes. In the various embodiments, the structural properties of the splines enable the respective splines, ablation electrodes and sensing electrodes to flexibly conform to the target cardiac tissue to enhance ablative energy delivery and provide high fidelity localized sensing of the tissue and the target treatment zones.

Figure 2F:
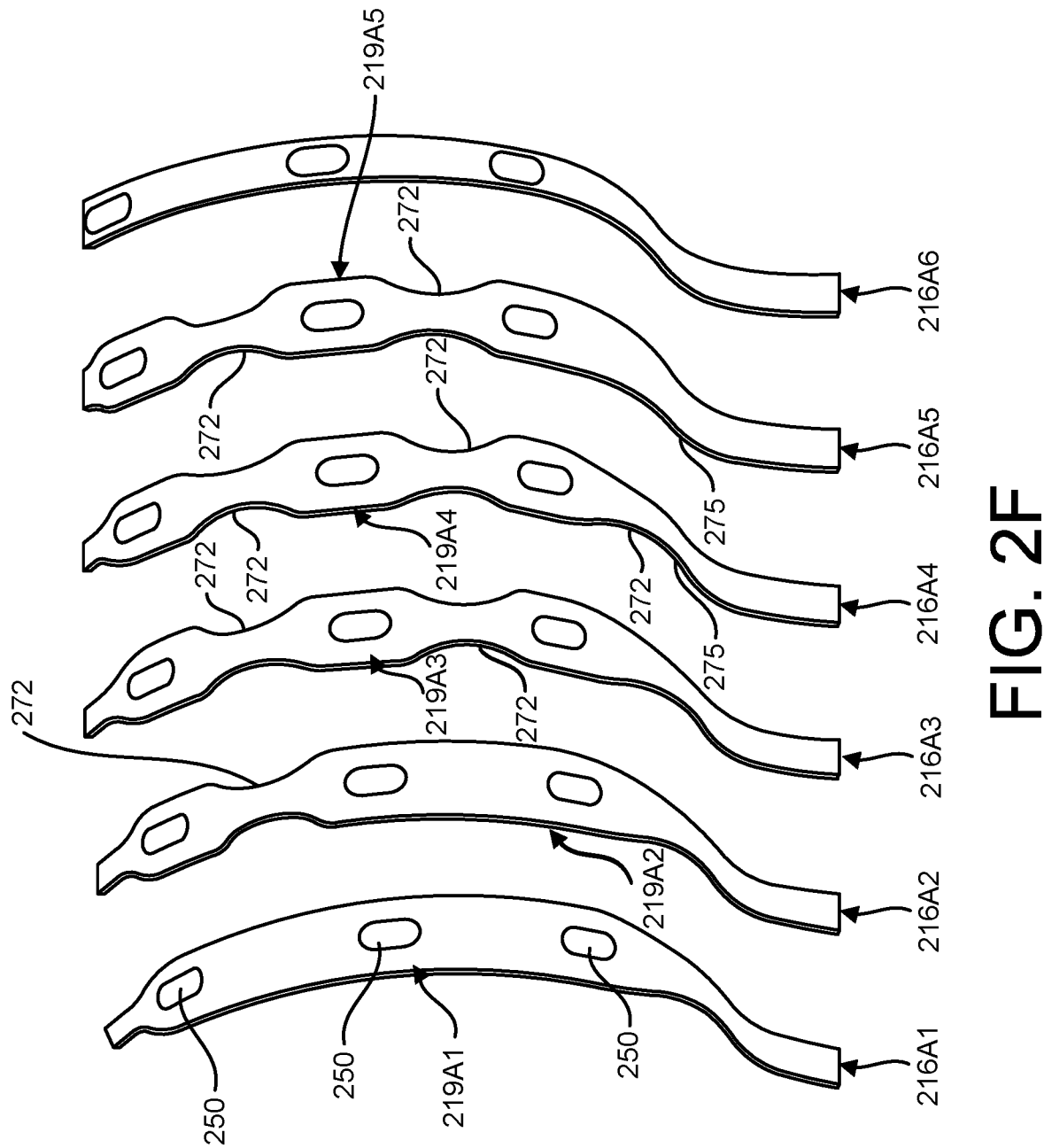
FIG. 2F is a schematic illustration of alternative designs of splines that may be used in the electrode assembly of FIGS. 2A-2C.

FIG. 2F schematically illustrates alternative designs of splines 216A1-216A5 that may be used in the electrode assembly 210 according to various embodiments, depicted in the configuration they assume when the electrode assembly 210 is fully expanded. The skilled artisan will appreciate that the splines 216A1-216A5 may be representative of the other splines forming the electrode assembly 210 in various embodiments. Overall, the various spline designs of FIG. 2F exhibit varying degrees of stiffness when the expanded electrode assembly 210 undergoes axial and/or radial compressive loads (e.g., when urged against cardiac tissue). As such, varying the structural features of the splines, as described in greater detail below, allows for customization of the shape of the electrode assembly 210 when under such loads. Additionally, the various spline designs depicted in FIG. 2F accommodate a range of ablation electrode geometries (and resulting active surface areas) for optimization of pulsed field ablation energy delivery. In the illustrated embodiment, for illustration purposes, the ablation electrode for each spline is omitted, and only spline sensing electrodes 250 are depicted so as to provide scale and context with respect to the locations of the various structural features described.

As shown in FIG. 2F, the spline 216A1 has an intermediate portion 219A1 that lacks any scalloped regions, and thus, the outer lateral edges of the intermediate portion 219A1 are generally straight or linear. In the illustrated embodiment, the intermediate portion 219A1 has a uniform width along its entire length. In general, the embodiment of the spline 216A1 is generally less flexible under radial or compressive loads than the other embodiments illustrated in FIG. 2F.

As further shown, the spline 216A2 has an intermediate portion 219A2 with a single scalloped region 272 interposed between two distal-most located spline sensing electrodes 250, with the more proximal region of the intermediate portion 219A2 having a generally uniform width along its length. The inventors of the present disclosure have discovered that the spline 216A2 will exhibit a reduction in overall stiffness under axial or radial compression of about 3.07% relative to the spline 216A1.

As further shown, the spline 216A3 has an intermediate portion 219A3 with two scalloped regions 272 each interposed between two adjacent spline sensing electrodes 250. The spline 216A3 may be constructed substantially similar to the splines 216A-216F illustrated in FIGS. 2A-2E and described in the corresponding text. The inventors of the present disclosure have discovered that the spline 216A3 will exhibit a reduction in overall stiffness under axial or radial compression of about 12.88% relative to the spline 216A1.

As further shown, the spline 216A4 has an intermediate portion 219A4 with two scalloped regions 272 each interposed between two adjacent spline sensing electrodes 250, and a third scalloped region 273 located in an intermediate-to-proximal transition region 275 located proximally of the proximal-most spline sensing electrode 250. The inventors of the present disclosure have discovered that the spline 216A4 will exhibit a reduction in overall stiffness under axial or radial compression of about 13.91% relative to the spline 216A1.

As further shown, the spline 216A5 has an intermediate portion 219A5 with two scalloped regions 272 each interposed between two adjacent spline sensing electrodes 250, similar to spline 216A3. The spline 216A5 differs from the spline 216A3 in that the intermediate-to-proximal transition region 275 has a width that uniformly decreases in the proximal direction. The inventors of the present disclosure have discovered that the spline 216A5 will exhibit a reduction in overall stiffness under axial or radial compression of about 9.41% relative to the spline 216A1.

Finally, the spline 216A6, provided for further context with respect to the aforementioned stiffness reductions, has a uniform width along its entire length (i.e., lacks any scalloped regions). The inventors of the present disclosure have discovered that the spline 216A6 will exhibit a reduction in overall stiffness under axial or radial compression of about 26.38% relative to the spline 216A1.

Figure 2G:
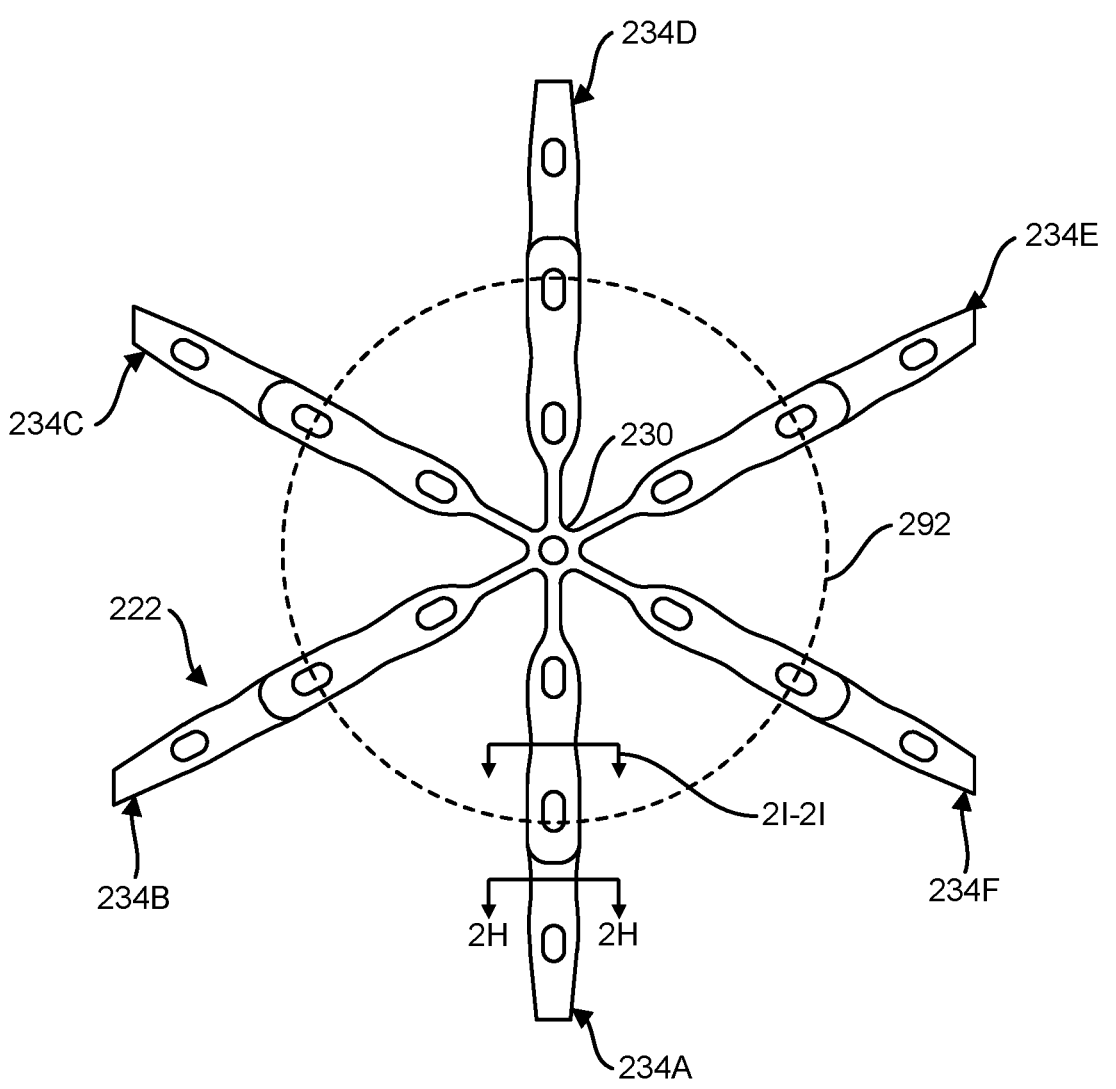
FIG. 2G is a partial plan view of an alternative electrode assembly for use in the catheter of FIG. 1 shown in two-dimensions to illustrate the layout thereof.
Figure 2H:
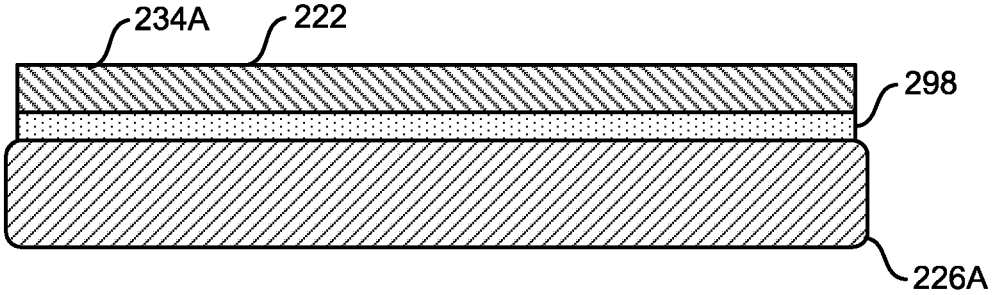
FIGS. 2H and 2I -2I are schematic cross-sectional illustrations of portions of the electrode assembly shown in FIG. 2G.
Figure 2I:
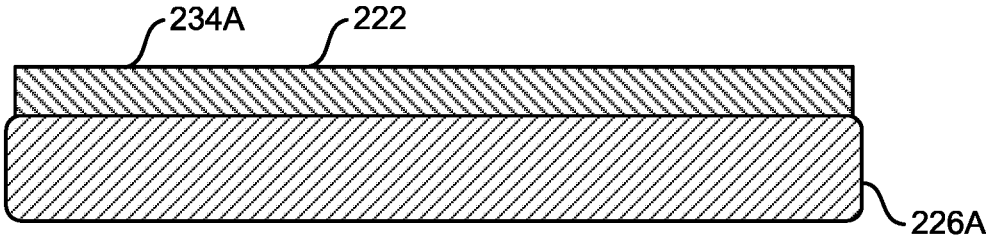

The structural/mechanical properties of the electrode assembly 210 can additionally, or alternatively, be tailored through techniques employed in its construction and formation. FIG. 2G is a partial plan view of the electrode assembly 210 shown in two-dimensions to illustrate the layout thereof, similar to that shown in FIG. 2C, except as described below, and FIGS. 2H and 2I are schematic cross-sectional views of portions of the electrode assembly 210 taken along lines 2H-2H and 2I-2I, respectively. For ease of illustration, the details of the construction of the flexible are omitted in FIGS. 2H and 2I.

The embodiment of FIG. 2G differs from that illustrated in FIG. 2C in that the electrode assembly 210 of FIG. 2G includes an unadhered region 292 (the region depicted within the dashed circle in FIG. 2G), in which the flex circuit hub 230 and the portions of the flex circuit splines 234A-234F located within the region 292 are not directly adhesively attached to the underlying support member 220. Thus, as shown in FIG. 2H, in regions outside the unadhered region 292, the flexible circuit includes an adhesive layer 298 interposed between and attaching the flex circuit branch 234A to the support member branch 226A. In contrast, within the unadhered region 292, no adhesive layer is present between flex circuit spline 234A and the support member branch 226A. In embodiments, the location of the boundary defining the region 292 may be selected based on the particular desired structural characteristics of the electrode assembly. In embodiments, the boundary of the region 292 may be located at the approximate equator (i.e., a location that is equidistant from the proximal and distal ends), or at the maximum diameter, of the expanded electrode assembly 210 (see FIG. 2A), although in other embodiments this boundary may be located at a different position. The omission of a direct mechanical attachment of the flexible circuit 222 to the support member 220 within the region 292 permits some relative motion between the support member 220 and the flexible circuit 222 in that region, which minimizes stresses transferred to the flexible circuit 222 under external axial or radial compressive loads. Accordingly, this design functions to reduce strain on the flexible circuit 222 when the electrode assembly 210 is inserted and retracted into a relatively small bore delivery sheath, with a corresponding reduction in plastic deformation of the flexible circuit 222, during use. The inclusion of the region 292 further tends to reduce the overall stiffness of the expanded electrode assembly 210, thus enhancing the degree in which it can elastically deform and conform to target tissue, e.g., the endocardial wall, during a pulsed field ablation and related mapping procedure.

Figure 4A:
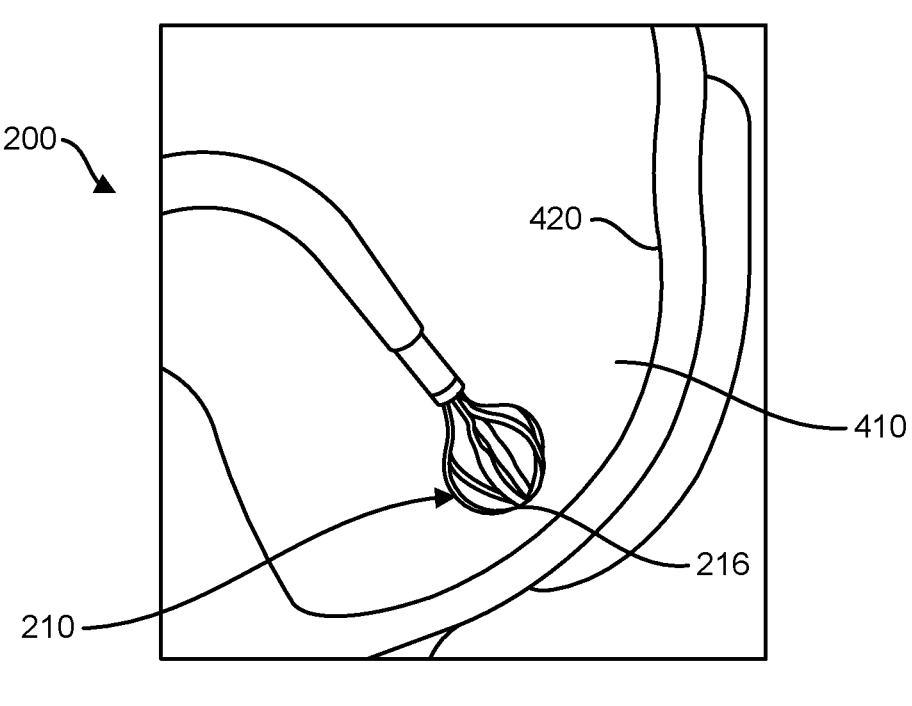
FIGS. 4A and 4B are illustrations of the distal portion of the catheter of FIG. 1 in exemplary use settings within a cardiac chamber of a patient, in accordance with embodiments of the subject matter of the disclosure.
Figure 4B:
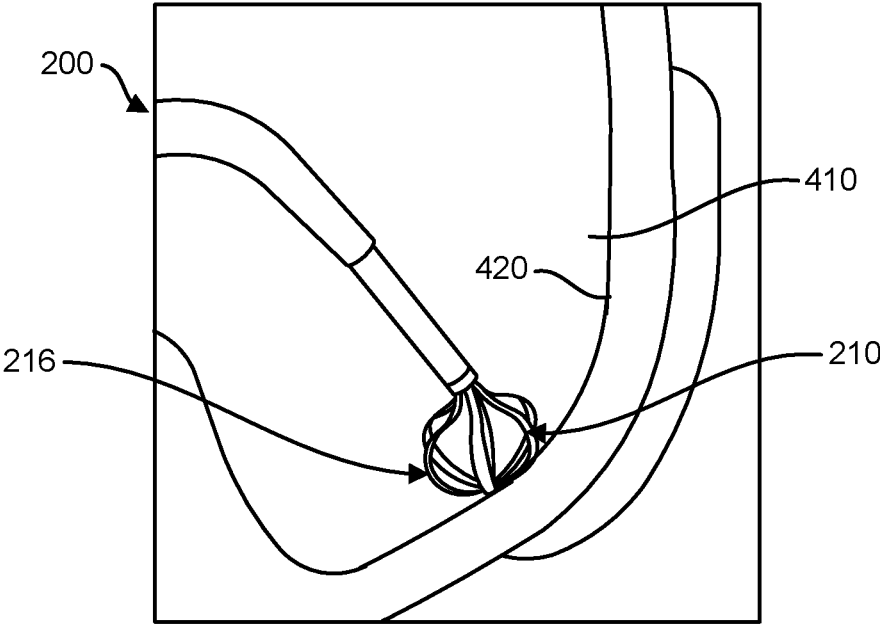

FIGS. 4A and 4B illustrate the functionality of the catheter 200, and in particular, the electrode assembly 210, in use in a cardiac procedure. As can be seen in FIG. 4A, the electrode assembly 210 can be positioned within a cardiac chamber of interest, e.g., the left atrium 410. When positioned within the blood pool of the left atrium 410, the electrode assembly 210 is pre-configured to assume its fully expanded shape. As shown in FIG. 4B, the design of the electrode assembly 210 allows the splines 216 to elastically deform when the electrode assembly 210 is urged into contact with the wall 420 of the cardiac chamber. The illustrated deformation results in maximizing the surface area of the ablation electrode 238 (and sensing electrodes 250) that are in contact with the target tissue without placing undesirable force on the cardiac wall 420. The flexibility of the electrode assembly 210 further results in its assumption of its undeformed expanded shape when it is retracted away from the cardiac wall 420.

It is well understood that methods that include one or more steps, the order listed is not a limitation of the claim unless there are explicit or implicit statements to the contrary in the specification or claim itself. It is also well settled that the illustrated methods are just some examples of many examples disclosed, and certain steps may be added or omitted without departing from the scope of this disclosure. Such steps may include incorporating devices, systems, or methods or components thereof as well as what is well understood, routine, and conventional in the art.

The connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112 (f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:
1. A catheter for ablating cardiac tissue through irreversible electroporation, the catheter comprising:
    a tubular outer shaft having a proximal end and an opposite distal end; and
    an electrode assembly extending distally from the distal end of the outer shaft, the electrode assembly comprising a flexible circuit having a distally located central flex circuit hub and a plurality of flex circuit branches extending proximally from the hub portion, each of the flex circuit branches defining, at least in part, an electrode assembly spline and including a proximal end portion attached to and constrained by the outer shaft, the flexible circuit further including an ablation electrode including an ablation electrode hub portion located on the flex circuit hub, and a plurality of ablation electrode branches integrally formed with the ablation electrode hub portion, each of the ablation electrode branches extending proximally along a portion of a respective one of the flex circuit branches and terminating in a proximal end.

2. The catheter of claim 1, wherein the flexible circuit further comprises a plurality of spline sensing electrodes located on each flex circuit branch, wherein one or more of the plurality of spline sensing electrodes on each flex circuit branch is disposed within a periphery of the respective ablation electrode branch on the flex circuit branch and is electrically isolated from the ablation electrode.

3. The catheter of claim 2, wherein one or more of the plurality of spline sensing electrodes is located proximal to the proximal end of the ablation electrode branch on each respective flex circuit branch.

4. The catheter of claim 3, wherein the flexible circuit further comprises a hub sensing electrode centrally located on the flex circuit hub.

5. A catheter for ablating cardiac tissue through irreversible electroporation, the catheter comprising:

a tubular outer shaft having a proximal end and an opposite distal end;

an electrode assembly extending distally from the distal end of the outer shaft, the electrode assembly defining a distally located central hub portion and a plurality of splines each including a distal end portion extending proximally from the central hub portion, a proximal end portion attached to and constrained by the outer shaft, and an intermediate portion between the proximal end portion and the distal end portion, the electrode assembly comprising:

a support member having a support member hub and a plurality of support member branches extending proximally from the support member hub;

a flexible circuit disposed over an outer surface of the support member and having a flex circuit hub disposed over the support member hub, and a plurality of flex circuit branches, each of the flex circuit branches disposed over a respective one of the support member branches, the flexible circuit further including an ablation electrode including an ablation electrode hub portion located on the flex circuit hub, and a plurality of ablation electrode branches integrally formed with the ablation electrode hub portion, each of the ablation electrode branches extending proximally along a portion of a respective one of the flex circuit branches and terminating in an ablation electrode proximal end.

6. The catheter of claim 5, wherein the flexible circuit further comprises a plurality of spline sensing electrodes located on each flex circuit branch, wherein one or more of the spline sensing electrodes on each flex circuit branch is disposed within a periphery of the respective ablation electrode branch disposed on the flex circuit branch and is electrically isolated from the ablation electrode.

7. The catheter of claim 6, wherein the proximal end of each ablation electrode branch has a contoured shape.

8. The catheter of claim 6, wherein one or more of the plurality of spline sensing electrodes is located proximal to the proximal end of the ablation electrode branch on the respective flex circuit branch.

9. The catheter of claim 6, wherein each ablation electrode branch includes one or more ablation electrode branch apertures formed therein, and wherein one of the spline sensing electrodes is disposed within a respective one of the ablation electrode branch apertures.

10. The catheter of claim 9, wherein each ablation electrode branch aperture is bounded by a respective inner peripheral surface of the ablation electrode branch, and wherein an outer peripheral surface of the spline sensing electrode disposed within the respective ablation electrode branch aperture is spaced from the respective inner peripheral surface of the ablation electrode branch.

11. The catheter of claim 10, wherein the intermediate portion of each spline includes one or more scalloped regions each having a scalloped region width that is smaller than the intermediate portion maximum width, and wherein at least one scalloped region is located in a portion of each spline on which a respective ablation electrode branch is located.

12. The catheter of claim 6, wherein the distal end portion of each spline has a distal portion maximum width, and the intermediate portion of each spline has an intermediate portion maximum width that is greater than the distal portion maximum width.

13. The catheter of claim 6, wherein the flexible circuit further includes a hub sensing electrode centrally located on the flex circuit hub.

14. The catheter of claim 6, further comprising one or more shaft electrodes located proximate the distal end of the tubular outer shaft.

15. The catheter of claim 14, wherein the ablation electrode and the one or more shaft electrodes are configured to define an anode/cathode electrode pair for delivery of electroporation ablation energy to target tissue.

16. A catheter for ablating cardiac tissue through irreversible electroporation, the catheter comprising:

a tubular outer shaft having a proximal end and an opposite distal end;

an electrode assembly extending distally from the distal end of the outer shaft, the electrode assembly defining a distally-located central hub portion and a plurality of splines each including a distal end portion extending proximally from the central hub portion, a proximal end portion attached to and constrained by the outer shaft, and an intermediate portion between the proximal end portion and the distal end portion, the electrode assembly comprising:

a support member formed from a superelastic material and having a support member hub and a plurality of support member branches integrally formed with and extending proximally from the support member hub;

a flexible circuit disposed over an outer surface of the support member and having a flex circuit hub disposed over the support member hub, and a plurality of flex circuit branches integrally formed with the flex circuit hub, each of the flex circuit branches disposed over a respective one of the support member branches, the flexible circuit further including:

an ablation electrode including an ablation electrode hub portion located on the flex circuit hub, and a plurality of ablation electrode branches integrally formed with the ablation electrode hub portion, each of the ablation electrode branches extending proximally along a portion of a respective one of the flex circuit branches; and a plurality of spline sensing electrodes, wherein one or more of the spline sensing electrodes is disposed within a periphery of each of the ablation electrode branches and is electrically isolated from the ablation electrode.

17. The catheter of claim 16, wherein the distal end portion of each spline has a distal portion maximum width, and the intermediate portion of each spline has an intermediate portion maximum width that is greater than the distal portion maximum width.

18. The catheter of claim 17, wherein the intermediate portion of each spline includes one or more scalloped regions each having a scalloped region width that is smaller than the intermediate portion maximum width, and wherein at least one scalloped region is located in a portion of each spline on which a respective ablation electrode branch is located.

19. The catheter of claim 18, wherein one or more of the plurality of spline sensing electrodes is located proximal to the proximal end of the ablation electrode branch on the respective flex circuit branch.

20. The catheter of claim 19, wherein the flexible circuit further includes a hub sensing electrode centrally located on the flex circuit hub.

* * * * *